US012578033B2

(12) United States Patent
Dharmadasa et al.

(10) Patent No.: US 12,578,033 B2
(45) Date of Patent: Mar. 17, 2026

(54) VALVE

(71) Applicant: Imperial College Innovations Limited, London (GB)

(72) Inventors: Asela Bandara Dharmadasa, London (GB); Nigel Stephen Blair, Suffolk (GB); Andrew Douglas McCulloch, Suffolk (GB); Manish Kumar Patel, London (GB); Carlos MH Gómez, London (GB)

( * ) Notice: Subject to any disclaimer, the term of this patent is extended or adjusted under 35 U.S.C. 154(b) by 881 days.

(21) Appl. No.: 17/798,006

(22) PCT Filed: Feb. 5, 2021

(86) PCT No.: PCT/GB2021/050261
§ 371 (c)(1),
(2) Date: Aug. 5, 2022

(87) PCT Pub. No.: WO2021/156629
PCT Pub. Date: Aug. 12, 2021

(65) Prior Publication Data
US 2023/0052770 A1 Feb. 16, 2023

(30) Foreign Application Priority Data
Feb. 7, 2020 (GB) .................................... 2001683

(51) Int. Cl.
*A61M 16/20* (2006.01)
*F16K 11/085* (2006.01)
*F16K 31/56* (2006.01)

(52) U.S. Cl.
CPC ......... *F16K 31/563* (2013.01); *A61M 16/201* (2014.02); *F16K 11/0853* (2013.01); *F16K 31/566* (2013.01)

(58) Field of Classification Search
CPC .......... A61M 16/0463; A61M 16/0816; A61M 16/20; A61M 16/833; A61M 16/201;
(Continued)

(56) References Cited

U.S. PATENT DOCUMENTS 2,311,464 A 2/1943 Parker
2,702,050 A 2/1955 Thomas
(Continued)

FOREIGN PATENT DOCUMENTS

CN 2112736 U 8/1992
CN 201502749 U 6/2010
(Continued)

OTHER PUBLICATIONS

Harriet Story, NHS Associate and Loanna Papacharalampous, NHS Technology Transfer associate, Imperial College London, Dated Aug. 28, 2019, TEEP Connector Ref: 6799, 7 pages.
(Continued)

*Primary Examiner* — Margaret M Luarca
(74) *Attorney, Agent, or Firm* — Bradley J. Thorson; DeWitt LLP

(57) ABSTRACT

A valve for use with breathing assistance apparatus comprises first, second and third ports (21, 22, 23) for respective connection to a patient breathing tube, a first ventilation apparatus and a second ventilation application. The valve includes a bistable valve mechanism having a first stable configuration in which the first port is in fluid communication with the second port and not the third port; and a second stable configuration in which the first port is in fluid communication with the third port and not the second port. The valve has an actuator configured to transition the bistable valve mechanism between the two stable configurations and preventing the valve mechanism from maintaining a stable intermediate position between the first and second stable
(Continued)

(2a)

(2b)          (2c)

configurations. In this way a patient may be switched from one ventilation apparatus to another ventilation apparatus without sudden loss of pressure in the disconnecting circuit causing potentially infected aerosols to be released, and the without sudden loss of positive end expiratory pressure to the patients lungs.

19 Claims, 11 Drawing Sheets

(58) Field of Classification Search
CPC   A61M 39/26; F16K 31/52466; F16K 31/003; F16K 31/566
See application file for complete search history.

(56) References Cited

U.S. PATENT DOCUMENTS

| | | | |
|---|---|---|---|
| 4,150,694 A | 4/1979 | Halpine | |
| 4,493,435 A | 1/1985 | Hartley | |
| 5,720,282 A | 2/1998 | Wright | |
| 5,746,199 A * | 5/1998 | Bayron | A61M 16/20 |
| | | | 128/205.24 |
| 10,279,137 B1 | 5/2019 | Morejon | |
| 2002/0117174 A1 | 8/2002 | Colas | |
| 2012/0048274 A1* | 3/2012 | Bayron | A61M 16/0833 |
| | | | 128/205.14 |
| 2014/0036049 A1 | 2/2014 | Miller | |
| 2016/0348795 A1 | 12/2016 | Gamache | |
| 2017/0059055 A1 | 3/2017 | Yu et al. | |
| 2017/0259023 A1 | 9/2017 | Venegas | |
| 2019/0013433 A1 | 1/2019 | Kim et al. | |

FOREIGN PATENT DOCUMENTS

| | | | |
|---|---|---|---|
| CN | 203154594 U | 8/2013 | |
| CN | 204774830 U | 11/2015 | |
| CN | 105805358 A | 7/2016 | |
| CN | 209959990 U | 1/2020 | |
| CN | 211536125 U | 9/2020 | |
| DE | 19539655 C1 | 9/1996 | |
| DE | 202013006445 U1 | 8/2013 | |
| EP | 0700687 A1 | 3/1996 | |
| EP | 3115073 B1 | 3/2018 | |
| JP | S4894696 | 11/1973 | |
| JP | H07236696 A | 9/1995 | |
| JP | 4523314 B2 | 8/2010 | |
| NL | 9301212 A | 1/1995 | |
| SU | 381812 A1 | 5/1973 | |
| WO | 9101771 A1 | 2/1991 | |
| WO | 2005003610 A1 | 1/2005 | |
| WO | 2016085807 A1 | 6/2016 | |
| WO | 2016182536 A1 | 11/2016 | |
| WO | 201810680 A1 | 1/2018 | |

OTHER PUBLICATIONS http://www.intersurgical.com/products/anaesthesia/monitoring-line-connectors.
https://www.intersurgical.com/content/files/80259/1200335970.
https://my.supplychain.nhs.uk/Catalogue/product/fdc849.
https://my.supplychain.nhs.uk/Catalogue/product/fdc881.
https://www.tri-anim.com/tee-adapter-nif-tee-non-rebreathing-pharm-33476-3756.aspx?search=26-33-3500EA.
https://www.tri-anim.com/connector-airlife-omni-flex-pediatric-15-mm-od-x-22-mm-od-expand-5-to-6.5-cm-pharm-23709-3756.aspx?search=04-3222EA.
https://www.tri-anim.com/y-connector-airlife-adult-elbow-ports-port-caps-22mm-od-x-22mm-od-x-15mm-id-pharm-34751-3756.aspx?search=04-001831.
http://www.mercurymed.com/catalogs/RDR_Connectors_Adapters.pdf.
https://www.tri-anim.com/valve-1-way-22mm-od-x-22mm-id-connections-low-flow-resistance-and-a-capped-monitoring-port-pharm-34381-3756.aspx?search=36-1644.
International Search Report for PCT/GB2021/050261 dated Apr. 28, 2021, 2 pages.
Search Report from corresponding application No. GB2111500.1 dated May 11, 2022, 4 pages.
Search Report from corresponding application No. GB2001683.8 dated Jul. 15, 2020, 1 page.
China National Intellectual Property Administration, First Office Action, for Chinese Patent Application No. 202180018355.1, Mar. 28, 2025, 22 pages. Amendments with English translation of Amended Claims for Japanese Patent pages.
Japanese Office Actions and Amendments with English translation of Amended Claims for Japanese Patent Application No. 2022-547822, 23 pages.
Communication under Rule 71(3) EPC from corresponding Application No. GB 21704921.2-1015 dated Sep. 1, 2023, 41 pages.
Intellectual Property Office, Patents Act 1977: Examination Report under Section 18(3) from corresponding application No. GB2001683.8 dated Sep. 1, 2023, 4 pages.

* cited by examiner (1a)

(1b)

(1c)

(1d)

(2c)

(2b)

(2a)

(4a)

(4b)

(4c)

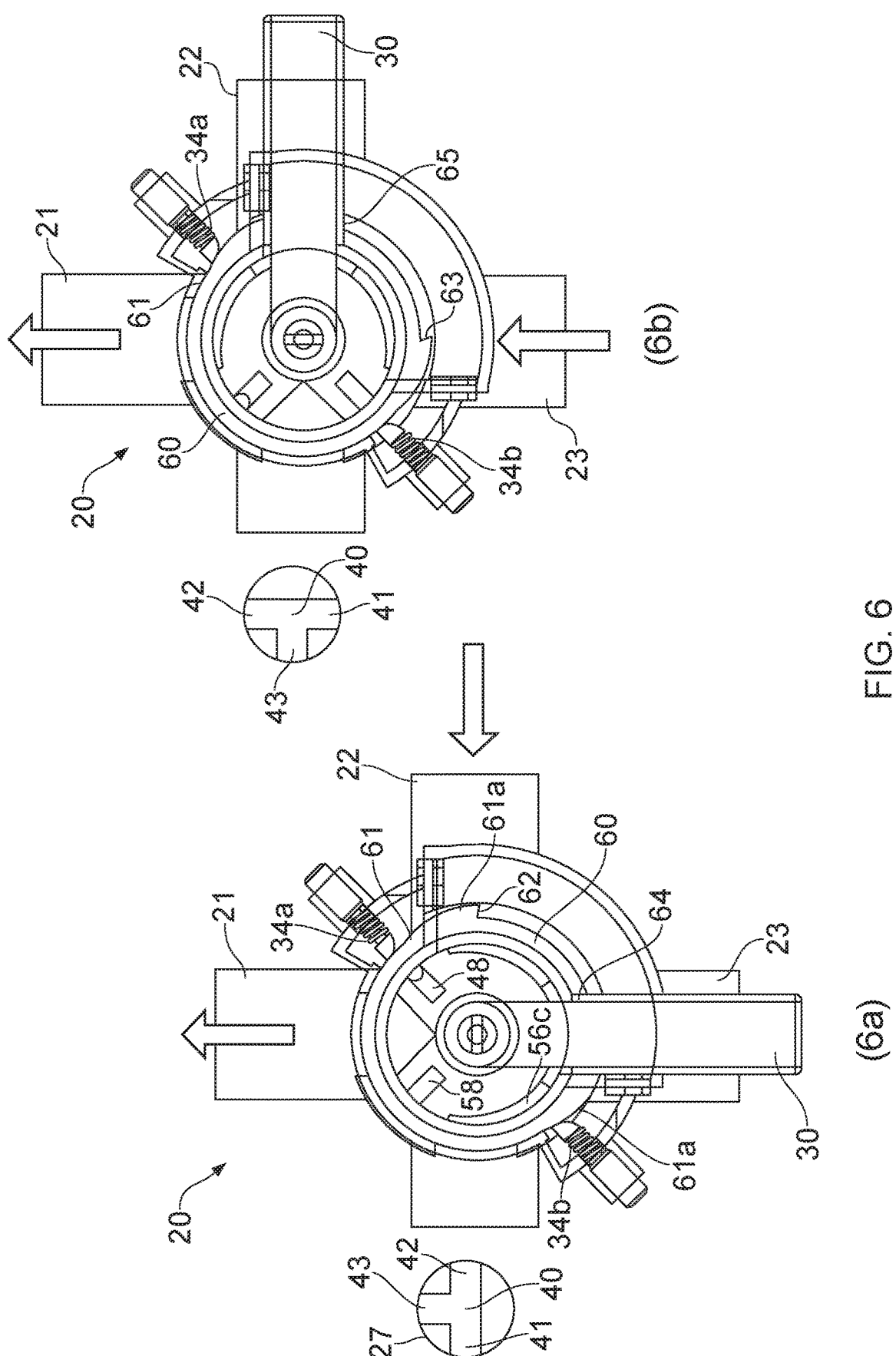
F I G. 6

VALVE

CROSS-REFERENCED TO RELATED APPLICATIONS

This application claims priority from Application PCT/GB2021/050261, filed Feb. 5, 2021, and claims priority from Great Britain Patent Application No. 2001683.8, filed Feb. 7, 2020, which is deemed incorporated by reference in its entirety in this application.

STATEMENT REGARDING FEDERALLY SPONSORED RESEARCH OR DEVELOPMENT

Not applicable.

BACKGROUND OF THE INVENTION

This disclosure relates to two-way valves and in particular though not exclusively to valves suitable for use with breathing assistance equipment and patient ventilator systems.

Critically ill patients often require artificial ventilation to assist or replace spontaneous breathing. This can be provided manually or via a mechanical ventilation system. Mechanical ventilation is termed "invasive" if it involves any instrument penetrating the mouth or the skin. There are two main modes of mechanical ventilation: positive pressure ventilation, where air (or another gas mix) is pushed into the trachea, and negative pressure ventilation, where air is, in essence, sucked into the lungs, e.g. by exerting a sub-atmospheric pressure on the external chest wall.

A patient may need to be temporarily disconnected from a breathing circuit and ventilator for a number of reasons, for example: (i) to change the ventilator e.g. to a portable ventilator for intra- and inter-hospital transfers; (ii) to manually ventilate the patient e.g. with a Water's circuit to improve oxygen saturations; (iii) to change the breathing circuit; (iv) to move or roll the patient.

There can be a number of problems associated with disconnecting a breathing circuit.

A first potential problem relates to staff safety. When a breathing circuit is disconnected, potentially infected aerosols of secretions and water within the breathing circuit can be released into the room (potentially under pressure) and attendant clinical staff or healthcare workers may be sprayed with these aerosols whilst temporarily disconnecting ventilated patients from their breathing circuit.

A second potential problem relates to patient safety. When a breathing circuit is opened to atmosphere, it becomes depressurized and the patient's lungs lose positive end expiratory pressure (PEEP). PEEP is required during ventilation to prevent the collapse of alveoli in the patient's lungs. If alveoli collapse, oxygen levels in the blood may drop and the collapsed alveoli may become more susceptible to infection. It can be difficult to re-inflate the alveoli. In patients with severe lung disease, when a breathing circuit is disconnected, it is not uncommon for the oxygen saturations to drop precipitously to dangerous levels within seconds. Historically, the loss of PEEP during breathing circuit disconnection was mitigated by applying a clamp to the endotracheal tube prior to and during disconnection, but this practice may have contraindications. If a patient makes an inspiratory effort whilst a clamp is applied, the negative pressure generated can lead to life threatening complications.

It is an object of the invention to provide an improved method and apparatus for mitigating some or all of the above problems.

According to one aspect, the present invention provides a valve comprising:

first, second and third ports;

a bistable valve mechanism having (i) a first stable configuration in which the first port is in fluid communication with the second port and not the third port and (ii) a second stable configuration in which the first port is in fluid communication with the third port and not the second port; and an actuator configured to transition the bistable valve mechanism between the two stable configurations and prevent the valve mechanism from maintaining a stable intermediate position between the first and second stable configurations.

The valve may be particularly suited for use with for breathing assistance apparatus, breathing assistance equipment and/or patient ventilator systems. The first port may be configured for connection to a patient airway maintaining device. The second and third ports may be each configured for connection to a ventilator breathing circuit or breathing assistance device. The first port may have a 22 mm tapered outer diameter connector surface. The second and third ports may each have a 22 mm tapered internal diameter connector surface. The bistable valve mechanism may comprise a moveable valve core defining a ported chamber for establishing fluid communication paths between selected ones of the first, second and third ports in each of the first and second stable configurations. The valve core may be coupled to and drivable by the actuator via a spring loading mechanism. The actuator may be configured to move from a first position relative to the valve core up to a first release position to load the spring loading mechanism, and to trigger transition of the valve core from the first stable configuration to the second stable configuration by the spring loading mechanism upon reaching the first release position. The actuator may be configured to move from a second position relative to the valve core up to a second release position to load the spring loading mechanism, and to trigger transition of the valve core from the second stable configuration to the first stable configuration upon reaching the second release position. The actuator may comprise at least a first locking pin engaged with the moveable valve core to lock the valve core in the first stable configuration. The actuator may be configured to disengage the first locking pin from the valve core upon reaching the first release position. The actuator may comprise a second locking pin engaged with the moveable valve core to lock the valve core in the second stable configuration. The actuator may be configured to disengage the second locking pin from the valve core upon reaching the second release position. The valve core may comprise a valve core rotatable about a valve axis. The actuator may comprise a lever rotatable about the valve axis, the lever being coupled to the valve core by a torsion spring between the lever and an axially extending peg on the valve core. The valve may further comprise a cam drive element disposed adjacent the valve core. The cam drive element may comprise a first cam surface engaging the first locking pin and a step feature engageable by the actuator as it approaches the first release position to drive the first locking pin to disengagement from the valve core when the actuator reaches the first release position. The valve core may further include a first pin ramp surface within a channel extending between a first deep end and a first pin-receiving hole at a shallow end. The valve core may further include a second pin ramp surface within a channel extending between a second deep end and a second pin-receiving hole at a shallow end. The first and second pin-receiving holes respectively may be configured to block further motion of the valve core beyond the respective bistable positions. At least one of the first, second and third ports may comprise a bore housing and an axially displaceable sealing member within the bore housing. The axially displaceable sealing member may have a face seal at one end for engagement with the valve core and a sliding seal for sliding engagement with the bore housing. The sealing member may be coupled to be driven from an extended position having said face seal engaged with the valve core when the actuator is in the first position to a retracted position when the actuator moves past the first release position. The sealing member may be coupled to be driven back to the extended position having said face seal engaged with the valve core as the valve core reaches the second stable configuration.

At least one of the first, second and third ports may comprise a bore housing and an axially displaceable sealing member within the bore housing having a face seal at one end for engagement with the valve core and a sliding seal for sliding engagement with the bore housing. The sealing member may be coupled: (i) to be driven from an extended position having said face seal engaged with the valve core when the actuator is in the first position to a retracted position when the actuator moves past the first release position, and (ii) to be driven back to the extended position having said face seal engaged with the valve core as the valve core reaches the second stable configuration. The sealing member may be coupled to be driven from an extended position having said face seal engaged with the valve core when the actuator is in the second position to the retracted position when the actuator moves past the second release position. The sealing member may be coupled to be driven back to the extended position having said face seal engaged with the valve core as the valve core reaches the first stable configuration. The face seal of the sealing member may be biased towards the valve core by a spring bias.

Each of the first, second and third ports may comprise a respective said bore housing and axially displaceable sealing member. The one or more axially displaceable sealing members may be driven by the actuator via a cam drive element disposed adjacent to the valve core.

The valve as described above may further include a ventilation apparatus couplable to at least one of the second and third ports. The valve as described above may further include an endotracheal tube couplable to the first port.

According to another aspect, the invention provides a method of configuring breathing assistance apparatus for a patient comprising:

providing a valve having: first, second and third ports; a bistable valve mechanism having (i) a first stable configuration in which the first port is in fluid communication with the second port and not the third port and (ii) a second stable configuration in which the first port is in fluid communication with the third port and not the second port; and an actuator configured to transition the bistable valve mechanism between the two stable configurations and preventing the valve mechanism from maintaining a stable intermediate position between the first and second stable configurations, coupling a patient breathing tube to the first port, coupling a first ventilation device to the second port, while the valve is in the first stable configuration, coupling a second ventilation device to the third port;

switching the valve to the second stable configuration; and disconnecting the first ventilation device from the second port.

DESCRIPTION OF THE DRAWINGS

Embodiments of the present invention will now be described by way of example and with reference to the accompanying drawings in which:

FIG. 2a shows a perspective view of a three-port bistable valve for use with patient breathing assistance apparatus;

FIG. 2b shows a top view of the three-port bistable valve of FIG. 2a;

FIG. 2c shows a bottom view of the three-port bistable valve of FIG. 2a;

FIG. 4a is a perspective view, from the side and above, of a rotatable valve core element of the bistable valve of FIG. 2a;

FIG. 4b is a perspective view, from the side and above, of a sectioned rotatable valve core element of the bistable valve of FIG. 2a;

FIG. 4c is a top view of the cross-section of the rotatable valve core element of FIG. 4b;

FIGS. 6a and 6b are schematic cross-sectional top views of the valve of FIG. 2a respectively in first and second bistable configurations;

FIG. 8a is a perspective schematic view of the valve of FIG. 2a illustrating various sealing features;

FIG. 8b is a partial cross-sectional side view of sealing features in FIG. 8a;

DETAILED DESCRIPTION

Figure 1:
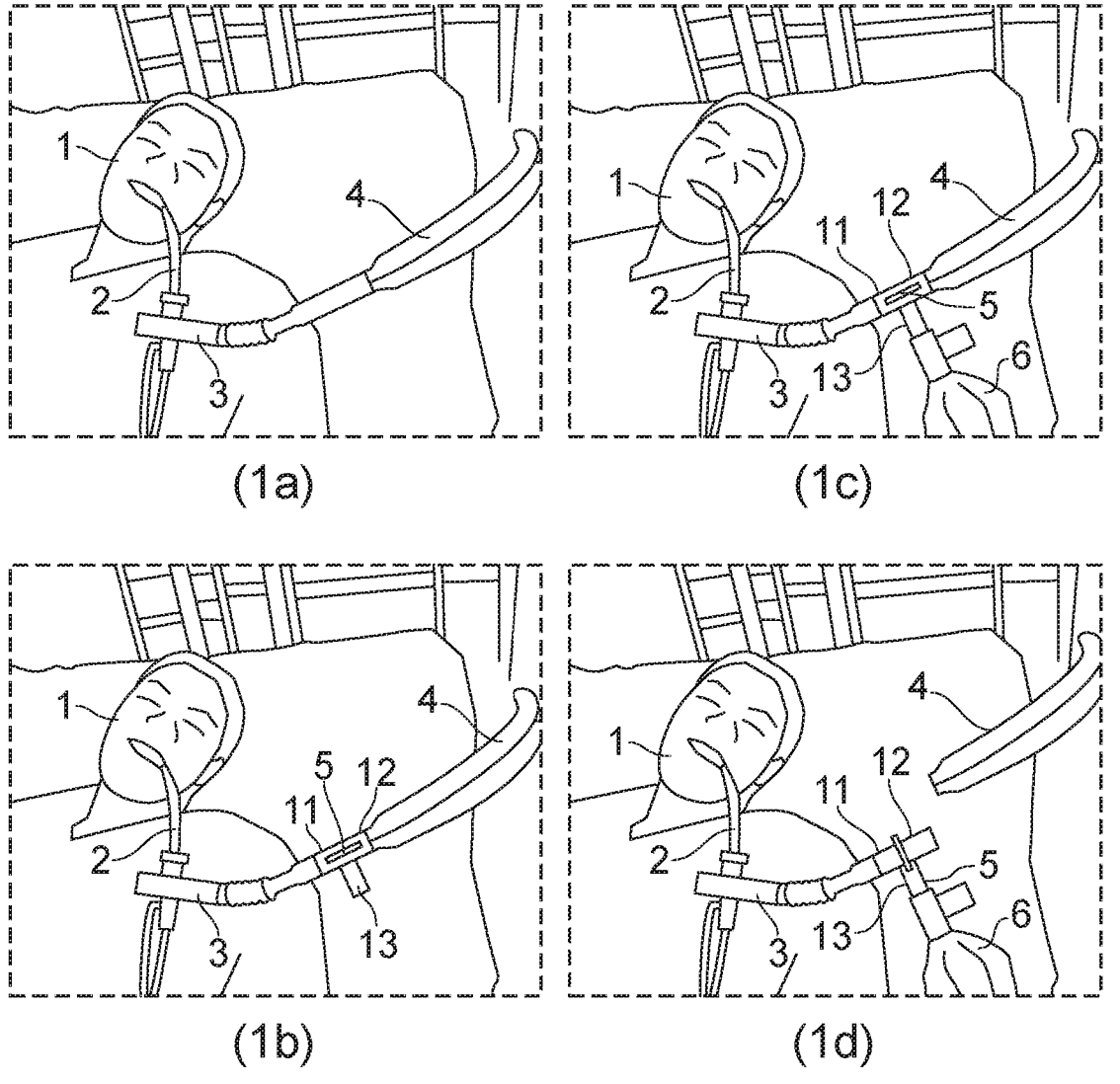
FIG. 1 shows a schematic diagram of a three-port connector in use with patient breathing assistance apparatus.

Throughout the present specification, the descriptors relating to relative orientation and position, such as "top", "bottom", "horizontal", "vertical", "left", "right", "up", "down", "front", "back", as well as any adjective and adverb derivatives thereof, are used in the sense of the orientation of a valve as presented in the drawings. However, such descriptors are not intended to be in any way limiting to an intended use of the described or claimed invention. The expression 'clockwise' and 'anticlockwise' are used herein in the sense of directionality as viewed from above the valve, for the purpose of illustration and explanation of specific embodiments as illustrated, and are not intended to limit to those specific embodiments.

FIG. 1 illustrates practical use of a patient ventilator system. As seen in FIG. 1*a*, patient 1 is provided with a breathing tube such as an endotracheal tube 2 placed through the mouth into the trachea to deliver oxygen and/or other gases to the lungs. Although the invention is described herein in connection with an endotracheal tube 2, other forms of breathing tube such as a tracheostomy tube can be applicable to the invention. A closed suction device 3 connects the patient to a ventilator breathing circuit 4. In circumstances as discussed above, it can be desirable to facilitate connection of the patient 1 to an alternative ventilation device, such as ventilation bag 6 (FIGS. 1*c* and 1*d*). This can be achieved using a T-shaped valve 5 as seen in FIG. 1*b* which has first branch 11 connected to the patient breathing tube 2 (via the suction device 3), a second branch 12 connected to the ventilator breathing circuit 4 and a third branch 13 suitable for connecting to a further ventilation device. In FIG. 1*b*, the T-shaped valve 5 has a valve mechanism rotated to a first configuration in which the first branch 11 is fluidly coupled to the second branch 12 by way of a first fluid passage and in which the third branch 13 is isolated from the first fluid passage between the first branch 11 and the second branch 12.

As seen in FIG. 1*c*, an alternative ventilation device 6 is coupled to the third branch 13 while the valve mechanism remains in the first configuration coupling the first branch 11 and the second branch 12.

As seen in FIG. 1*d*, the valve mechanism is then rotated to a second configuration in which the first branch 11 is fluidly coupled to the third branch 13 by way of a second fluid passage and in which the second branch 12 is isolated from the second fluid passage between the first branch and 11 and the third branch 13. In this configuration, the ventilator breathing circuit 4 is then disconnected as seen in FIG. 1*d*. The disconnection occurs after the patient's airway has been connected to the third branch 13 of the T-shaped valve and thus to the alternative ventilation device 6 and isolated from the ventilator breathing circuit 4.

In one aspect, a valve suitable for implementation in the context of FIGS. 1*a*-1*d* may have a mechanism in which the transition from the first configuration to the second configuration occurs quickly such that the valve does not remain, for any appreciable period of time, in an intermediate position between the first configuration and the second configuration. The expression "intermediate position" may encompass a position in which fluid communication between the first branch 11 and the second branch 12 and the third branch 13 might coexist simultaneously, or a position in which there is no fluid communication between any of the first branch 11, the second branch 12 and the third branch 13 (the fluid pathway between each of the first, second and third branches is blocked). The expression "any appreciable length of time" may be understood to be relative to the normal pressure changes within a patient's airway. In another aspect, a valve suitable for implementation in the context of FIGS. 1*a* to 1 *d* may have a mechanism in which a user cannot statically position or leave the valve in such an intermediate position.

Figure 2:
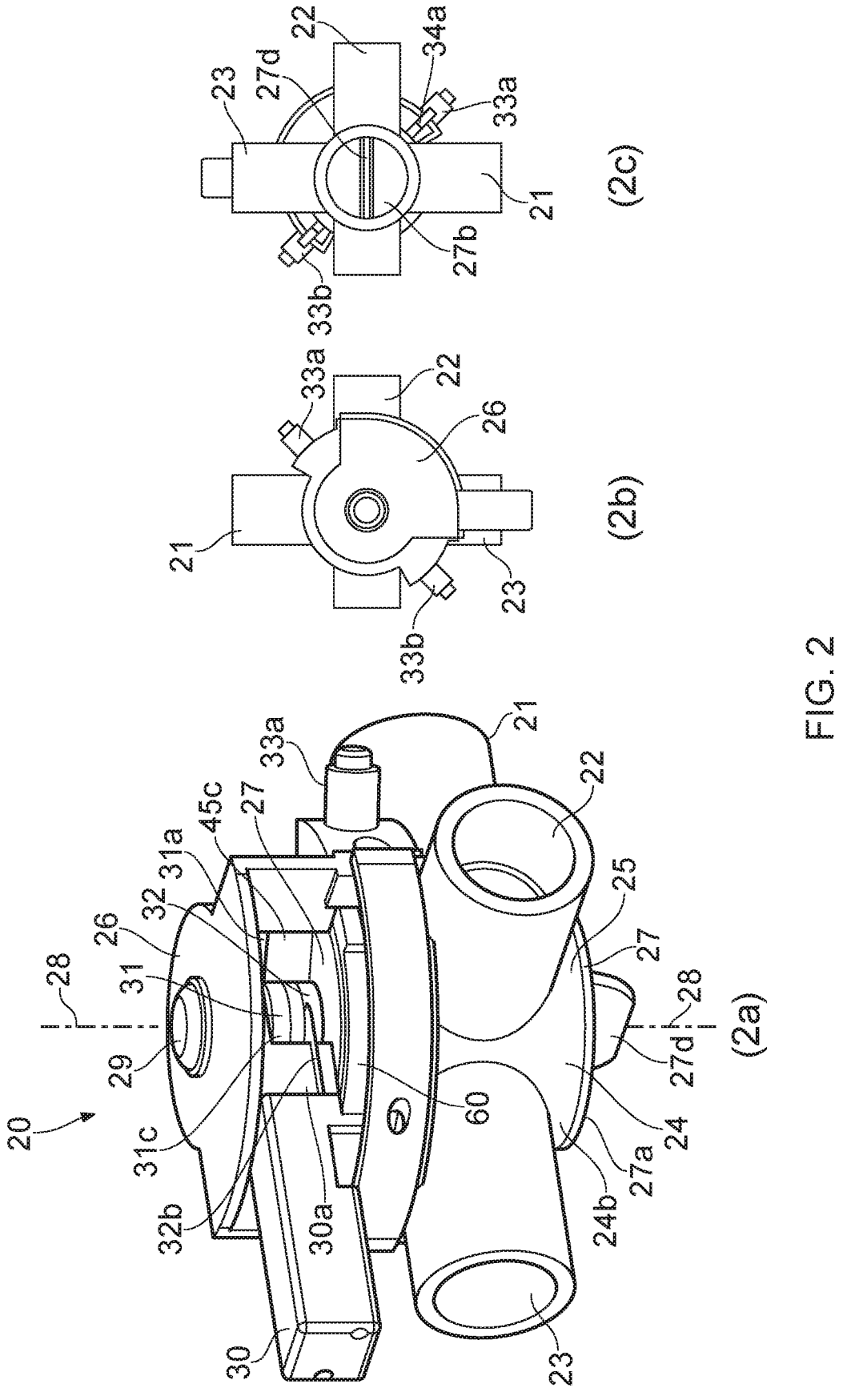
Figure 3:
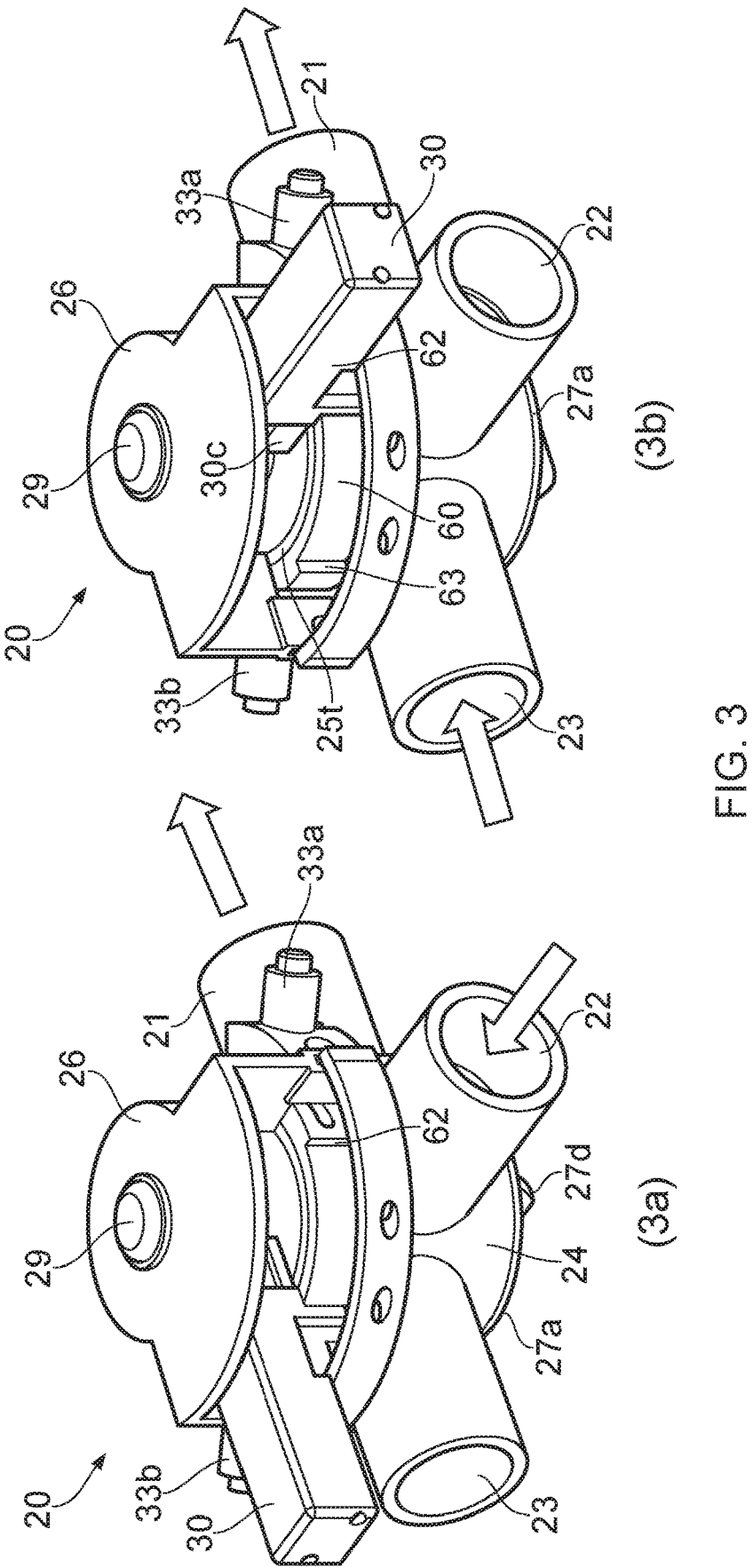
FIG. 3a shows a perspective view of the bistable valve of FIG. 2a in a first stable configuration and FIG. 3b shows a perspective view of the bistable valve of FIG. 2a in a second stable configuration.

With reference to FIGS. 2*a*-2*c*, a valve 20 suitable for the above purposes is described.

Valve 20 comprises a valve body 25 defining three ports 21, 22, 23 extending radially outward from a cylindrical core portion 24 of the valve body 25 and a top cover 26 extending axially upward from the core portion 24 of the body 25. Rotatably mounted within the core portion 24 is a valve core 27 which is rotatable about a valve axis 28 and secured to the top cover 26 by a securing feature 29 such as a screw, rivet, pin or other device which allows rotation of the valve core

27 relative to the valve body 25 but prevents axial displacement of the valve core relative to the valve body along the valve axis 28. The valve core 27 has a flanged base portion 27*b* with flange 27*a* extending radially outwards to cover the cylindrical bottom end 24*b* of the core portion 24 and be in sliding engagement therewith as the valve core rotates within the body 25. The base portion 27*b* of the valve core 27 may also include a direction indicator 27*d* disposed thereon which can provide a visual indication of the state of rotation of the valve core 27 externally of the body 25. In the arrangement shown, the direction indicator 27*d* comprises a lug extending axially downwards from the base portion 27*b* and extending diametrically across the base portion 27*b*. The direction indicator 27*d* could alternatively be provided by way of an embossed surface or surface marking on the base portion 27*b*, for example.

Figure 4:
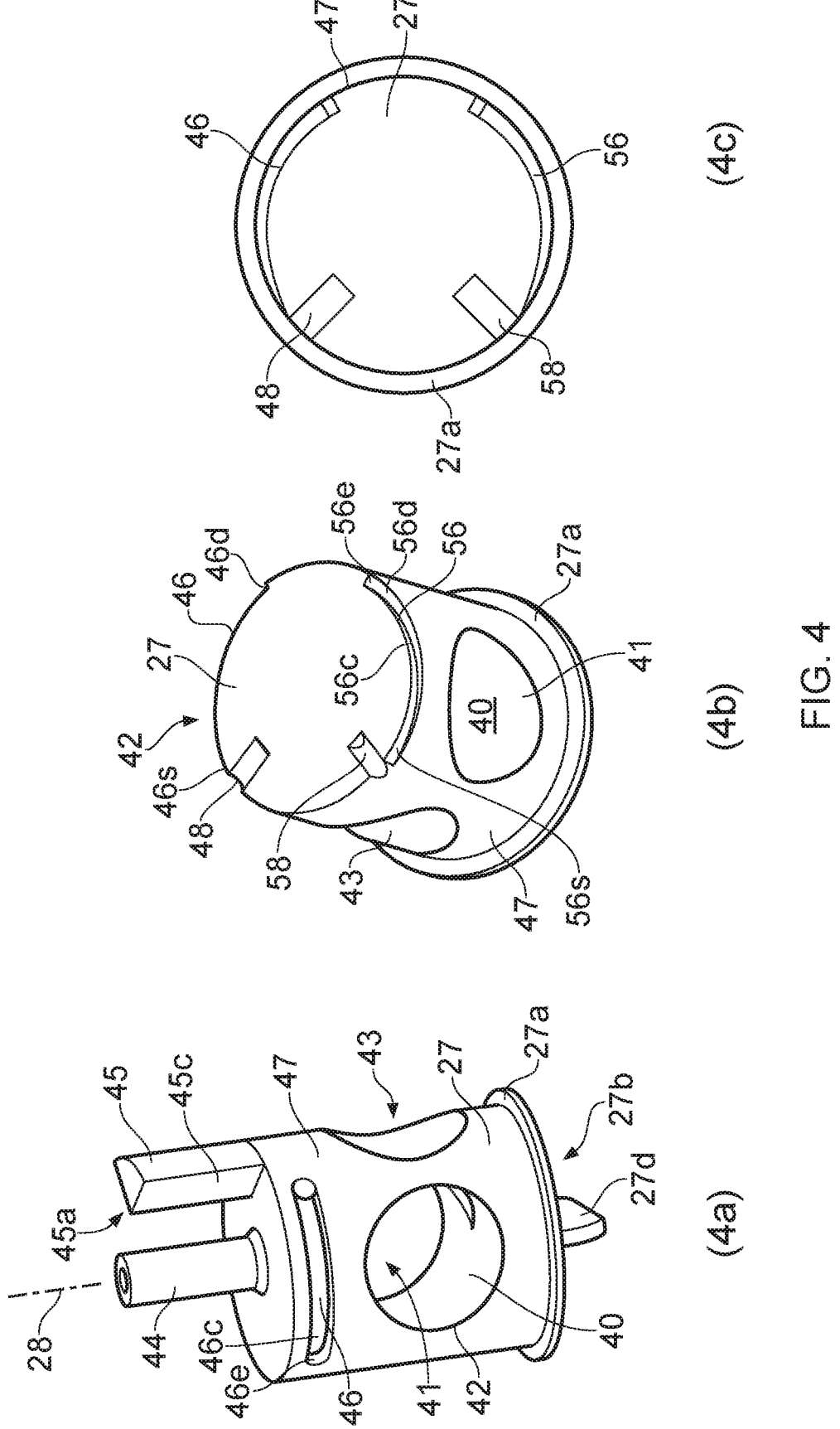

As best seen with reference to FIGS. 4*a* to 4*c*, the valve core 27 defines a ported chamber 40 having openings 41, 42, 43 respectively at 0, 180 and 90 degree positions relative to one another about the valve axis 28. These openings 41, 42, 43 are positioned to generally align with selected ones of the ports 21, 22, 23 when in certain angular positions within the valve body 25, as will be discussed later.

Also seen in FIG. 4*a* is a central shaft 44 extending axially upwards to engage with the securing feature 29 (FIG. 2*a*) when the valve core 27 is installed within the body 25. Also seen in FIG. 4*a* is a peg 45 extending in an axially upward direction parallel to the central shaft 44 and radially displaced therefrom. The peg 45 has a clockwise-facing surface 45*c* and an anticlockwise-facing surface 45*a*. Also provided on the valve core 27 is a pin ramp 46 comprising a channel or groove 46*c* cut into the circumferential surface 47 of the valve core. The channel 46*c* has a depth which varies as a function of circumferential position on the valve core 27 and terminates at a shallow end 46*s* with a locking pin hole 48 and terminates at a deep end 46*d* with a step surface 46*e*.

As seen in the cross-sectional views of the valve core 27 in FIGS. 4*b* and 4*c*, a further pin ramp 56 comprising a channel or groove 56*c* is cut into the circumferential surface 47 of the valve core 27 and the channel 56*c* also has a depth which varies as a function of circumferential position on the valve core 27 and terminates at a shallow end 56*s* with a locking pin hole 58 and terminates at a deep end 56*d* with a step surface 56*e*.

Returning to FIG. 2*a*, the valve 20 further comprises an operating lever 30 which is rotatable about the valve axis 28 and extends radially outwards from the top cover 26. The operating lever 30 is rotatable about the valve axis 28 relative to both the valve core 27 and the top cover 26, but in the arrangement shown, motion of the operating lever 30 is limited to an arc of approximately 90 degrees. The operating lever 30 is coupled to the valve core 27 by way of a pair of torsion springs 31, 32. The upper torsion spring 31 comprises a coil portion 31*c* around the valve axis 28, i.e. around the central shaft 44 (FIG. 4*a*) and a first arm 31*a* which bears against the clockwise-facing surface 45*c* of the peg 45 (just visible in FIG. 2*a* and fully visible in FIG. 4*a*), and a second arm 31*b* (visible in FIGS. 8*a* and 9) which is engaged with the operating lever 30, e.g. affixed to or disposed within the lever 30 on or below the clockwise facing surface 30*c* of the operating lever 30. The lower torsion spring 32 comprises a coil portion 32*c* around the valve axis 28, i.e. around the central shaft 44 (FIG. 4*a*) and a first arm 32*a* which bears against an anticlockwise-facing surface 45*a* of the peg 45, and a second arm 32*b* which is engaged with the operating lever 30, e.g. affixed to or disposed within the lever on or below the anticlockwise-facing surface 30*a* of the operating lever 30. In this way, the operating lever 30 is capable of applying both clockwise and anticlockwise rotational forces to the valve core 27 while still being capable of rotational motion relative to the valve core 27, for reasons to be explained hereinafter.

Figure 5:
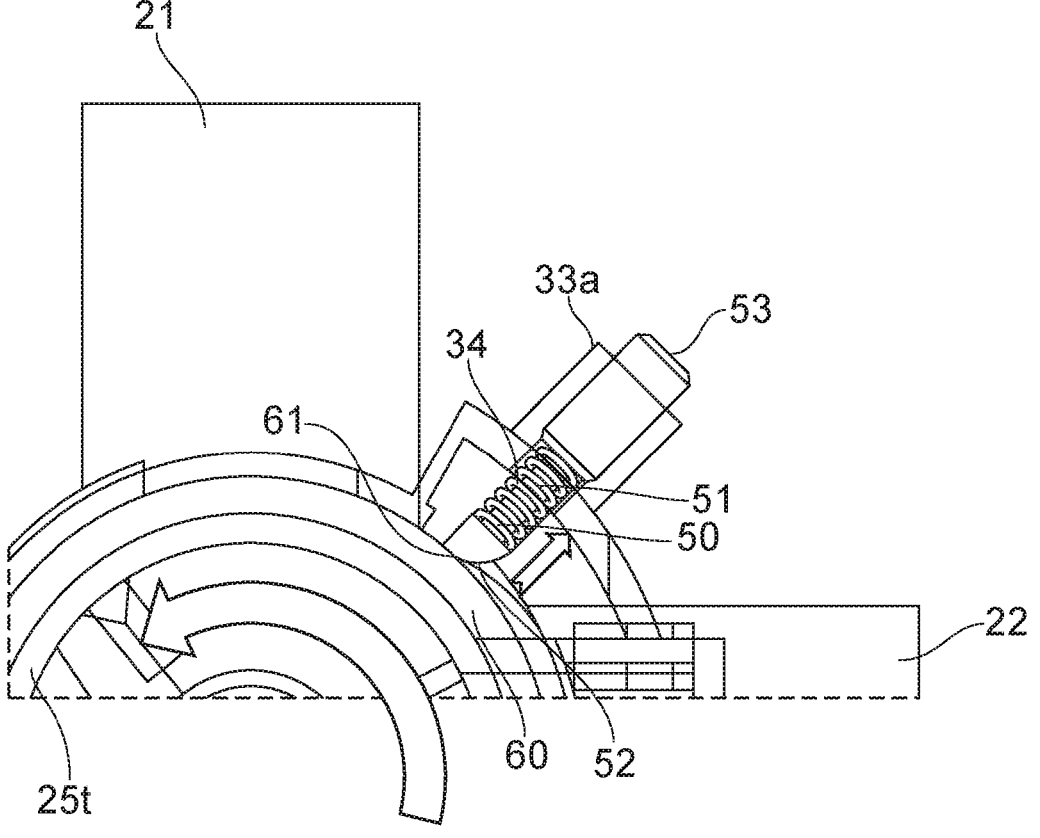
FIG. 5 is a partial cross-sectional schematic top view of the valve of FIG. 2a useful in illustrating features of the bistable mechanism.

With further reference to FIGS. 2*a* to 2*c*, the top cover 26 of the valve 20 further includes pin mounts 33*a* and 33*b* respectively supporting a first locking pin 34*a* and a second locking pin 34*b*. As best seen in FIG. 5, each locking pin 34 is displaceable along its axis which corresponds to a radial direction relative to the valve axis 28. Each locking pin 34 comprises a shaft 50, a biasing spring 51, a cam shoulder 52 and a spring adjustment screw mount 53. The cam shoulder 52 bears against the cam surface 61 of a cam ring 60 which extends around the valve core 27. The inner circumferential surface of the cam ring 60 is rotatable around, e.g. in sliding engagement with, an outer circumferential surface of a top portion 25*t* of the valve body 25. The cam ring 60 and the top portion 25*t* of the valve body 25 have elongate slots 80 therein (visible in FIGS. 8*a* and 9) through which the shaft 50 of the respective locking pin 34 can pass to enter the respective locking pin hole 48, 58 when the locking pin 34 is spring-biased towards a radially inward position. As most clearly seen in FIG. 9, the cam shoulder 52 of the locking pin 34 may be guided into a radially outward position when the cam shoulder 52 rides up a raised cam surface 61*a* and the cam shoulder 52 of the locking pin may be guided into a radially inward position when the cam shoulder 52 rides down the cam surface to a low cam surface 61*b*. In this way, the locking pin shaft 50 may be released from engagement with a respective pin hole 48, 58 of the valve core 27 to facilitate rotation of the valve core 27 about its axis.

As seen in FIGS. 6*a* and 6*b*, the cam ring 60 has a cam surface 61 which defines two raised cam surfaces 61*a* which are operable to lift the respective first and second locking pins 34*a*, 34*b* out of the respective locking pin holes 48, 58, and also two oppositely facing step features 62, 63. Clockwise-facing step feature 62 is engageable with an anticlockwise facing engagement surface 64 of the operating lever 30 (FIG. 6*a*), and anticlockwise-facing step feature 63 is engageable with a clockwise-facing engagement surface 65 of the operating level 30 (FIG. 6*b*).

FIGS. 6*a* and 6*b* show the valve 20 respectively in the first and second configurations. In FIG. 6*a*, the valve 20 is in a first stable configuration in which the first port 21 is in fluid communication with the second port 22 via the ported chamber 40 of the valve core 27, because opening 43 is in alignment with the first port 21 and opening 42 is in alignment with second port 22. See the inset schematic of valve core 27 showing its relative rotation position. It can also be seen that the third port 23 is blocked or occluded by the valve core 27 and therefore not in fluid communication with either the first port or the second port.

In FIG. 6*b*, the valve 20 is in a second stable configuration in which the first port 21 is in fluid communication with the third port 23 via the ported chamber 40 of the valve core 27, because opening 42 is in alignment with the first port 21 and opening 41 is in alignment with third port 23. Opening 43 is occluded. See the inset schematic of valve core 27 showing its relative rotation position. It can also be seen that the second port 22 is blocked or occluded by the valve core 27 and therefore not in fluid communication with either the first port or the third port. It can be understood from this diagram that in performing the quarter-turn anticlockwise rotation of the valve core 27 when transitioning from the configuration of FIG. 6*a* to the configuration of FIG. 6*b*, dependent on the diameters of the openings 41-43 and the ports 21-23, and on the circumference of the valve core 27/cylindrical core portion 24, the valve 20 can be configured as either a "break-before-make" type valve where the fluid flow from one port pair is completely shut off before the other fluid pair communication starts to be made, or vice versa ("make-before-break").

In FIG. 6*a*, first locking pin 34*a* is engaged with the corresponding locking pin hole 48, preventing rotation of the valve core 27. The second locking pin 34*b* may be positioned over the deep end 56*d* of the channel 56*c*, near the step surface 56*e*, in the valve core 27. It will be understood that the valve core 27 cannot rotate until the first locking pin 34*a* is released from its locking pin hole 48.

In FIG. 6*b*, second locking pin 34*b* is engaged with the corresponding locking pin hole 58, preventing rotation of the valve core 27. The first locking pin 34*a* may be positioned over the deep end 46*d* of the channel 46*c*, near the step surface 46*e*, in the valve core 27. It will be understood that the valve core 27 cannot rotate until the second locking pin 34*b* is released from its locking pin hole 58.

Now also referring to FIG. 7*a*, the operation of the valve will now be described.

Figure 7:
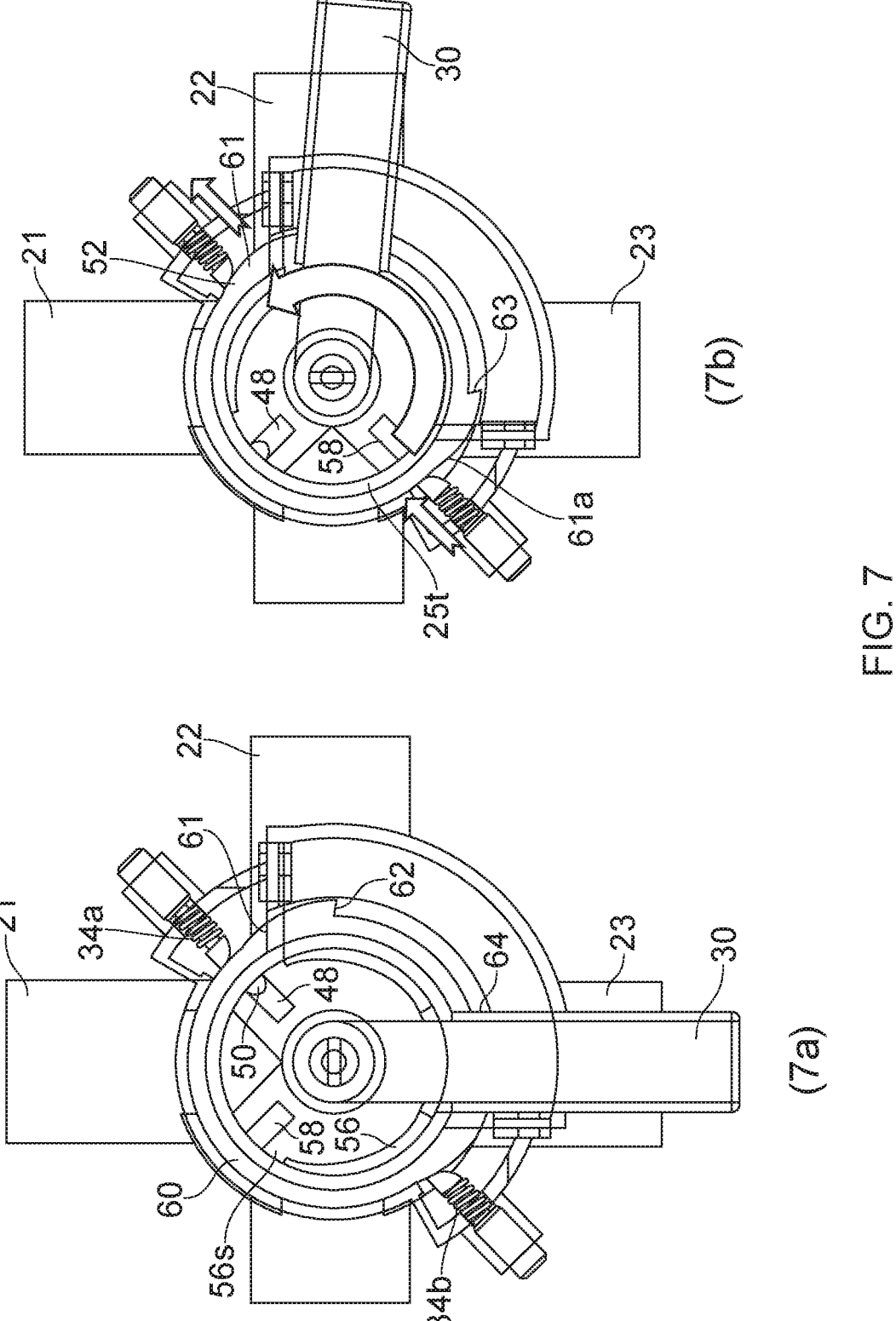
FIGS. 7a and 7b are schematic cross-sectional views of the valve of FIG. 2a illustrating respectively the first configuration and a transition towards the second configuration.

From the position of FIGS. 6*a* and 7*a*, the operating lever 30 is moved in an anticlockwise direction through approximately 90 degrees. During the course of that movement, which occurs against the bias of the upper torsion spring 31, the spring 31 stores considerable potential energy which strongly biases the valve core 27 for an anticlockwise rotation to follow the lever 30 motion. However, the first locking pin 34*a* prevents any such rotation of the valve core 27. However, just prior to the end of the 90 degree anticlockwise motion of the lever 30, the anticlockwise facing engagement surface 64 of the lever 30 engages the clockwise facing step feature 62 of the cam ring 60 causing the cam ring 60 to also rotate in an anticlockwise direction. The raised cam surface 61 drives the first locking pin 34*a* radially outward by engagement with the cam shoulder 52 thereby disengaging the locking pin shaft 50 from the locking pin hole 48 and thereby causing the valve core 27 to rapidly rotate in an anticlockwise direction under the accumulated spring bias in upper torsion spring 31. As the valve core 27 rotates, the second locking pin 34*b* travels up the pin ramp 56 to the shallow end 56*s* where it drops in to the locking pin hole 58. Further rotation of the valve core 27 is prevented by the second locking pin 34*b* dropping into the locking pin hole 58.

The sudden release of load on the operating lever 30 after the first locking pin 34*a* release is sufficient to ensure that the lever 30 reaches the fully anticlockwise position where it is stopped by the top cover 26.

A corresponding reverse movement of the operating lever 30 through approximately 90 degrees clockwise from the position of FIG. 6*b* uses the second (lower) torsion spring 32, the anticlockwise facing step feature 63 of the cam ring 60, and the second raised cam surface 61*a* to pre-load the second torsion spring 32 and then disengage the second locking pin 34*b* to trigger a corresponding reverse snap rotational movement of the valve core 27 from the stable position of FIG. 6*b* back to the stable position of FIG. 6*a*.

Thus, the valve 20 exemplifies a bistable valve mechanism having (i) a first stable configuration in which the first port 21 is in fluid communication with the second port 22 and not the third port 23 and (ii) a second stable configuration in which the first port 21 is in fluid communication with the third port 23 and not the second port 22. Furthermore, the operating lever 30 and associated features exemplifies an actuator which is configured to transition the bistable valve mechanism between the two stable configurations while preventing the valve mechanism from maintaining a stable intermediate position between the first and second stable configurations. The expression 'fluid communication' is intended to encompass arrangements in which air or other gas flow between the communicating ports 21, 22, or 23 via the valve core 27 is sufficient in volume and sufficiently unimpeded to have little or no impact on the operation of a breathing circuit delivering gas to a patient's lungs via a breathing tube.

The valve 20 thereby further exemplifies a bistable valve mechanism which comprises a moveable valve core 27 defining a ported chamber 40 for establishing respective fluid communication paths between the first and second or third ports 21, 22, 23 in the first and second stable configurations, where the valve core 27 is coupled to and drivable by the actuator lever 30 via a spring loading mechanism exemplified by the torsion springs 31, 32, peg 45 and cam ring 60. The raised cam surfaces 61a of the cam ring 60 and their action on the respective locking pins 34a, 34b respectively determine first and second release positions to trigger transition of the valve core 27 from the first stable configuration to the second stable configuration, using the spring loading mechanism, upon reaching the first release position, and vice versa.

The valve 20 described above can be configured to act as a patient breathing circuit connector and may be configured for particular use with standardised patent assisted breathing apparatus. This may include providing standard fittings on each of the first, second and third ports 21, 22, 23. For example, the first port 21 may be configured for connection to a patient airway maintaining device/breathing tube such as an endotracheal tube 2 or a tracheostomy tube, or via a suction device 3 connected thereto. In this respect, the first port 21 may preferably comprise a male connector with a conical 22 mm outer diameter connector surface with a 1:40 taper and an internal co-axial conical connector with a 15 mm internal diameter (female) conical connector with a 1:40 taper.

The second port 22 may be configured for connection to a ventilator 4 via breathing circuit tubing and can be left open to air when not in use. The second port 22 may comprise a female connector with a conical 22 mm internal diameter connector surface with a 1:40 taper. The third port 23 may be configured for connection to a second breathing circuit 6 and can also be left open to air when not in use. The third port 23 may comprise a female connector with a conical 22 mm internal diameter connector surface with a 1:40 taper. In this respect, the valve may be specifically configured to be compatible with relevant national and/or international standards, such as ISO 5356-1:2004 or ISO 5356-1:2015 specifying dimensional and gauging requirements for cones and sockets intended for connecting anaesthetic and respiratory equipment, e.g. in breathing systems, anaesthetic-gas scavenging systems and vaporizers.

The operating lever 30 allows switching from one breathing circuit 4 to another breathing circuit 6 while maintaining a closed circuit, thus preventing the release of potentially infected aerosols and minimizing the loss of positive end-expiratory pressure (PEEP) from the circuit. The valve may preferably be formed as a T-shaped device with ports at 90/180 degree relative angles, though other angular dispositions of the ports can be envisaged. The valve is preferably made principally from strong, lightweight plastic, e.g. with injection moulded parts, and is preferably a disposable device used for a single patient and for a limited period of time, e.g. up to a few days. Example materials may include polyethylene and polystyrene butadiene.

The valve preferably transitions from one bistable state to the other bistable state in a period of time which is very small compared to the period of normal pressure changes within a patient's airway, e.g. substantially less than 1 second and preferably substantially less than 0.2 second.

The valve arrangements as described herein provide fast-acting transitions with a decisive and unambiguous snap action which provides strong haptic and audible feedback when the valve transitions between its bistable states. This is particularly useful in the clinical context for ensuring ease of use in a potentially noisy and confusing environment. As a further safety feature, the direction indicator 27d also provides clear visual feedback as to the status of the valve and cannot show an ambiguous intermediate indication as it is integrally formed with the bistable valve core 27.

Figure 8:
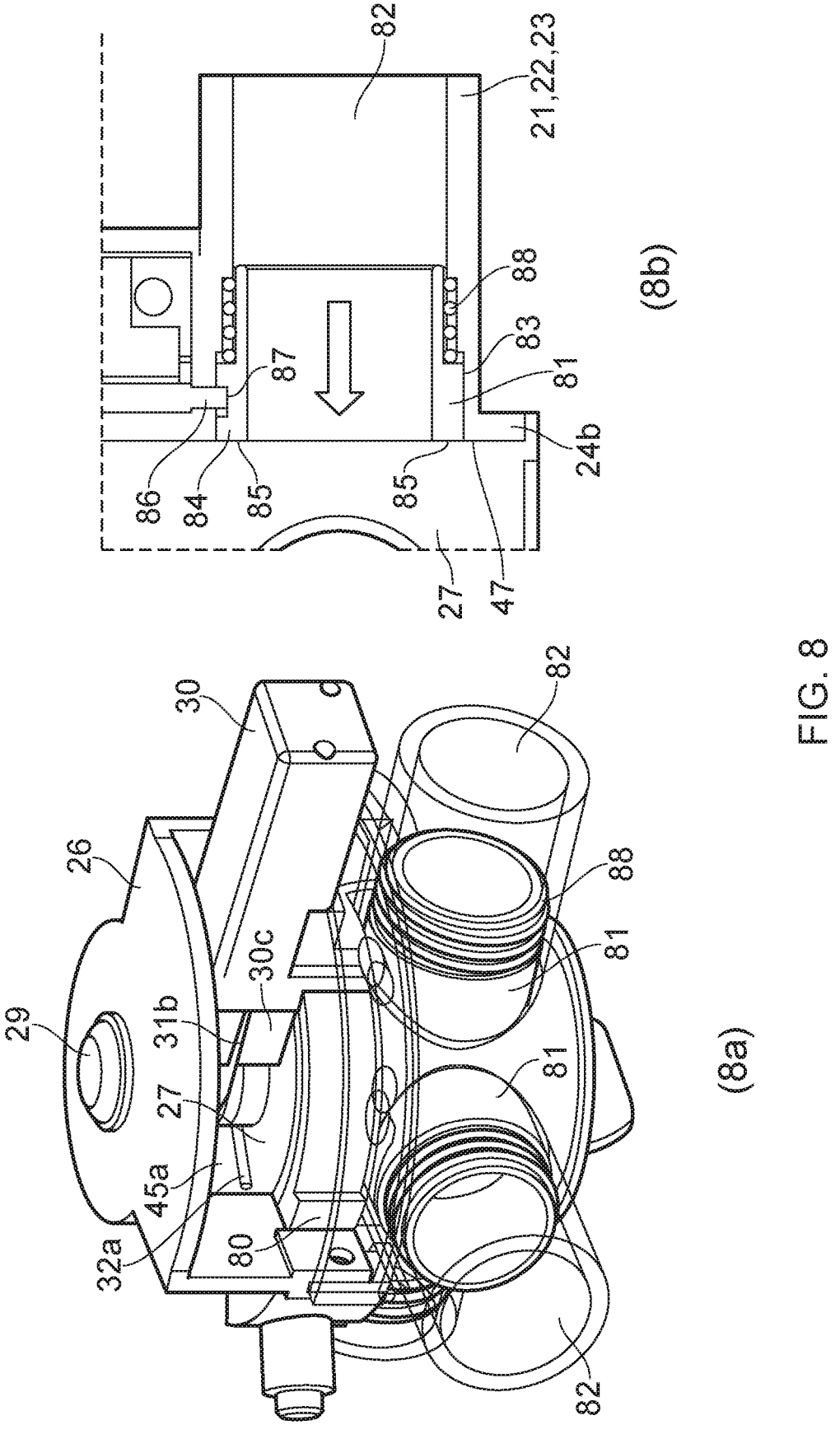
Figure 9:
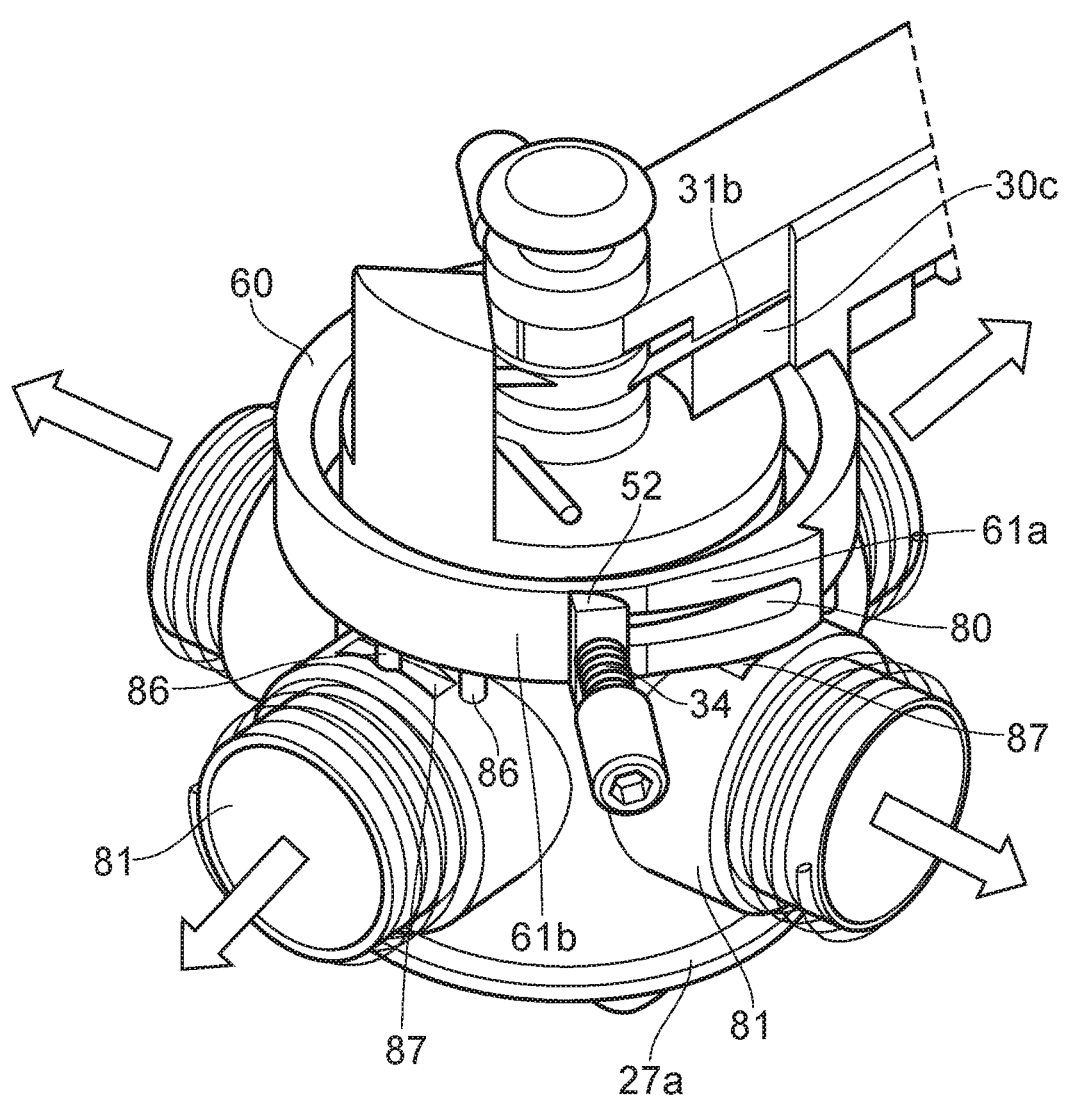
FIG. 9 is a perspective view of components of the valve in FIG. 8a with the body and top cover removed, revealing operation of those components.

Various modifications and adaptations may be made to the valve 20 as described above. FIGS. 8a, 8b and 9 illustrate a modification that incorporates higher performance sealing of the ports 21, 22, 23 to the valve core 27. As best seen in the cross-sectional view of FIG. 8b, one or more (and preferably all) of the first port 21, second port 22 and third port 23 may comprise an axially displaceable sealing member 81 which is configured to slide (left/right as viewed in FIG. 8b) within a bore housing 82. A sliding seal 83 provides a sealing interface between the sealing member 81 and the bore housing 82 and a spring 88 biases the axially displaceable sealing member 81 towards the valve core 27. The axially displaceable sealing member 81 also includes an inner end 84 defining a face seal 85 which is brought into sealing engagement with the circumferential surface 47 of the valve core 27 when the sealing member 81 is in the (biased) extended position as shown in FIG. 8b. Drive pins 86 (see also FIG. 9) extend downwardly from the cam ring 60 and each engages in a respective profiled slot 87 defining a cam surface in the axially displaceable sealing member 81. Referring to FIG. 9, as the cam ring 60 rotates under the action of the operating lever 30 (previously described), a respective drive pin 86 on the cam ring 60 engages the profiled slot 87 and, as the cam ring 61 rotates approaching a release position, the drive pin 86 momentarily drives the axially displaceable sealing member 81 away from the valve core 27 so that it can rapidly rotate with minimal friction and impedance. Upon reaching the stable configuration, the spring bias from springs 88 will bias the displaceable sealing members 81 into contact again with the valve core 27.

Figure 10:
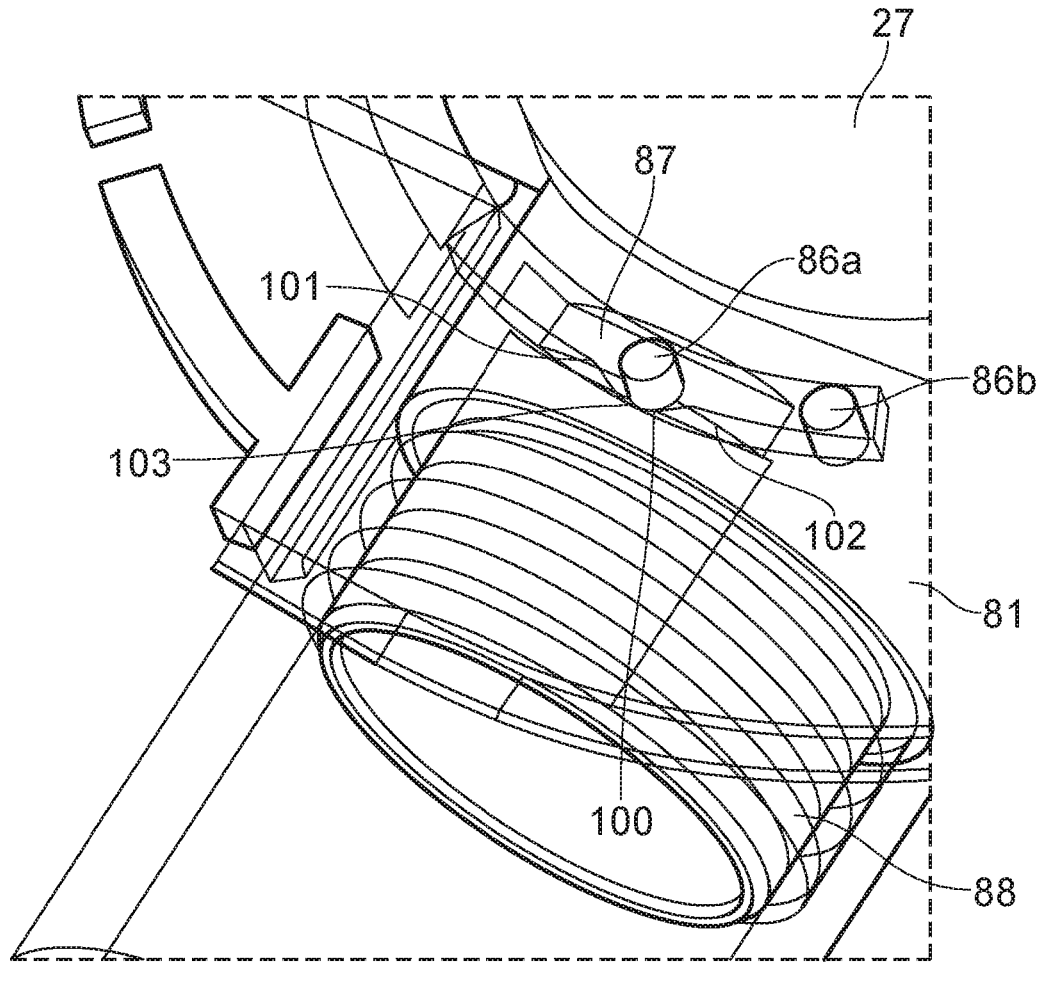
FIG. 10 is a perspective schematic view of components of the sealing features of FIGS. 8a and 8b.
Figures 11A, 11B, 11C:
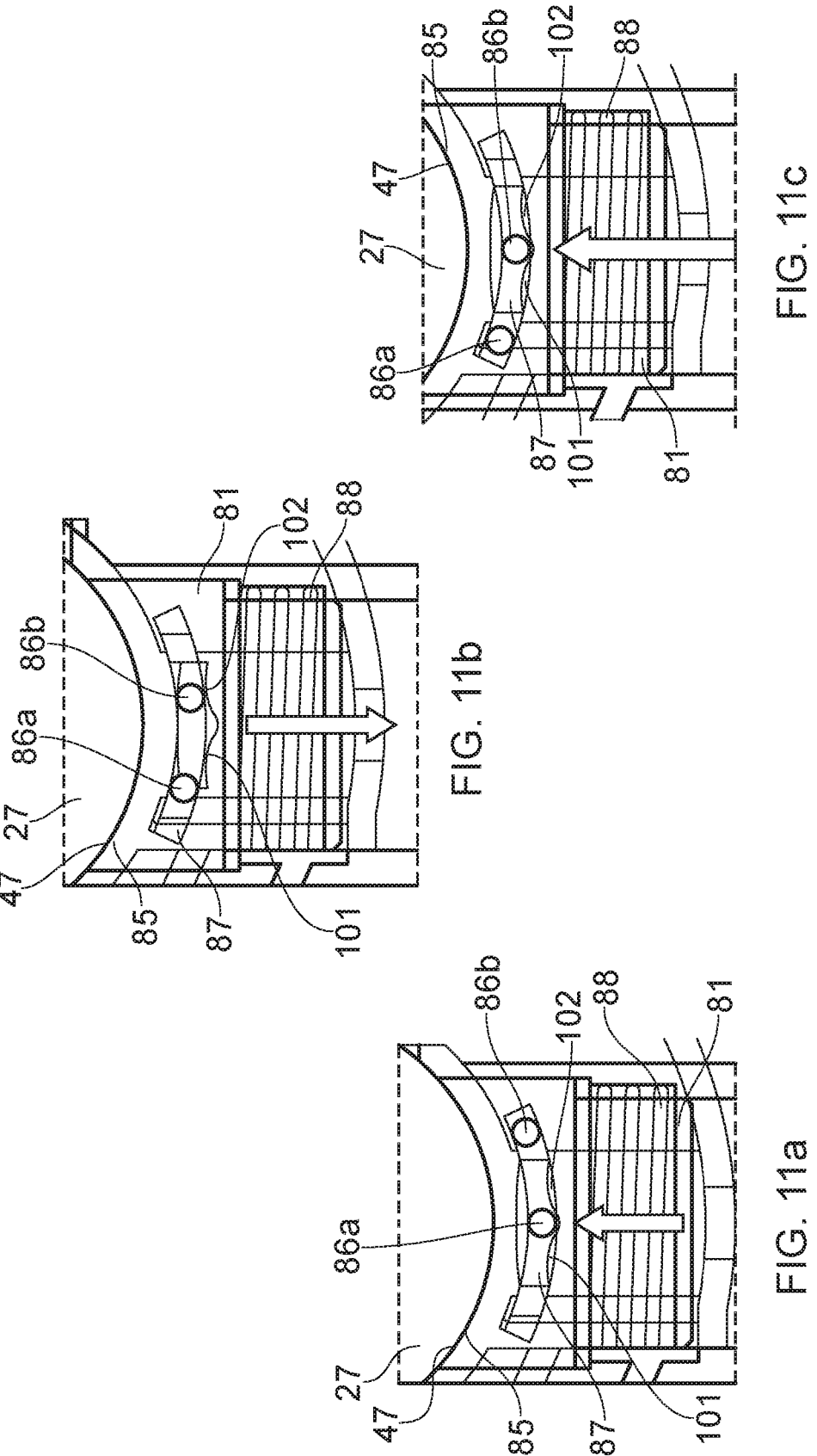
FIGS. 11a to 11c show plan views of the sealing features of FIG. 10 during various stages of operation.

Further detail of the profiled slot 87 and the operation of the axially displaceable sealing member 81 is described with reference to FIGS. 10 and 11. The profiled slot 87 in the axially displaceable sealing member 81 defines a cam surface 100 having first and second peak portions 101, 102 separated by a trough portion 103. With the valve 20 in one of the first and second stable configurations, the positions of the first and second drive pins 86a, 86b of the cam ring 60 are, respectively, aligned with the trough portion 103 and outside the profiled slot 87. The drive pins 86a, 86b do not touch, or do not bear against, the side walls of the profiled slot 87 and thus the sealing member is biased against the valve core 27 under the bias of spring 88, thereby effecting the best possible seal. This is applicable to all the axially displaceable sealing members 81 disposed around the valve core 27. As the operating lever 30 is rotated to the position at which it engages the cam ring (FIG. 7b) at the release position, and the cam ring 60 also starts to rotate, the cam ring pins 86a, 86b start to move from the rest positions (FIG. 11a) to a position in which they engage the peak portions 101, 102 of the profiled slot 87 (FIG. 11b), thereby pushing the axially displaceable sealing member 81 away from the valve core 27 against the bias of spring 88. The face seal 85 is disengaged from the surface 47 of the valve core 27 thus reducing the resistance to motion of the valve core 27. The valve core 27 rapidly rotates and the operating lever 30/cam ring 60 rapidly complete their rotations leaving the cam ring pins 86a, 86b in the positions as seen in FIG. 11c. In this configuration, the first drive pin 86a has passed beyond the profiled slot 87 and the second drive pin 86b is aligned with the trough portion 103, and the displaceable sealing member 81 has been biased once again against the valve core 27 by the spring 88. A corresponding reverse action takes place when the operating lever 30 is rotated back to the first position.

In a preferred arrangement as seen in FIG. 9, the valve 20 may be formed effectively with four bore housings 82 at 90 degree intervals around the body 25, each with an axially displaceable sealing member 81. In the three-port valve described above, one of the four bore housings 82 can be blanked off. This arrangement keeps the sealing arrangements symmetrical around the valve core 27, and may avoid the need for seals between the valve core 27 and the body 25, potentially reducing friction for a fast acting bistable valve.

In the embodiments shown herein, a three-port valve configuration is shown exemplifying a bistable valve mechanism in which a first port can be connected to either one of a second and third port by a rapidly transitioning valve mechanism. It will be understood that further ports could be added, and the actuator mechanism supplemented with a third position e.g. to provide a tristable valve mechanism. Such a tristable valve could have a position in which the first port can be connected to any one of a second, third or fourth port, or there could be a third stable position corresponding to a full isolated position where the first, second and third ports are all isolated from one another. In this respect, the expression 'bistable valve' is intended to encompass a valve having at least a first and a second stable configuration in which an intermediate stable position between the first and second stable configurations is prevented, but need not exclude the possibility of having a further stable configuration while still meeting the specified bistable requirements.

Although the embodiments of valve described in connection with the drawings are based on a bistable valve mechanism and actuator mechanism which rotate about an axis, it will be understood that the bistable functionality could also be achieved in other ways, e.g. with a valve mechanism deploying linear motion. For example, the valve could be configured as a Y-shaped valve with the stem of the Y-shape corresponding to the first port and the two branches of the Y-shape corresponding to the second and third ports. A linear sliding bistable mechanism may be used to transition the valve from a first configuration in which the first port is in fluid communication with the second port to a second configuration in which the first port is in fluid communication with the third port.

For the purposes of providing low cost disposable valves, the valves herein are preferably manually operated valves and constructed from low cost components. However, other electrically actuated versions may be envisaged.

The valve as described above can be deployed to more safely switch a patient using a breathing support tube and connected to a first ventilation device to a second ventilation device with reduced risk of the problems identified above. The patient's breathing tube is coupled to the first port of the valve and the first ventilation device is coupled to the second port and the breathing apparatus is operated with the valve in the first stable configuration. While the valve is in the first stable configuration, a second ventilation device may be coupled to the third port. The valve may then be switched to the second stable configuration. After the transition of the valve to the second stable configuration the first ventilation device may be disconnected from the second port which has been isolated from the patient's active breathing circuit.

Other embodiments are intentionally within the scope of the accompanying claims.

The invention claimed is:

1. A breathing assistance connector valve comprising:
first, second and third ports;
a bistable valve mechanism having (i) a first stable configuration in which the first port is in fluid communication with the second port and not the third port and (ii) a second stable configuration in which the first port is in fluid communication with the third port and not the second port; and
an actuator configured to transition the bistable valve mechanism between the two stable configurations and prevent the valve mechanism from maintaining a stable intermediate position between the first and second stable configurations, in which the bistable valve mechanism comprises a moveable valve core that is rotatable about a valve axis and defines a ported chamber for establishing fluid communication paths between selected ones of the first, second and third ports in each of the first and second stable configurations, the valve core being coupled to and drivable by the actuator via a spring loading mechanism, the actuator being configured to move from a first position relative to the valve core up to a first release position to load the spring loading mechanism, and to trigger transition of the valve core from the first stable configuration to the second stable configuration by the spring loading mechanism upon reaching the first release position.

2. The valve of claim 1 in which the actuator is configured to move from a second position relative to the valve core up to a second release position to load the spring loading mechanism, and to trigger transition of the valve core from the second stable configuration to the first stable configuration upon reaching the second release position.

3. The valve of claim 1 in which the actuator comprises at least a first locking pin engaged with the moveable valve core to lock the valve core in the first stable configuration, the actuator configured to disengage the first locking pin from the valve core upon reaching the first release position.

4. The valve of claim 1 in which the actuator comprises a lever rotatable about the valve axis.

5. The valve of claim 4, wherein the lever is coupled to the valve core by a torsion spring between the lever and an axially extending peg on the valve core.

6. The valve of claim 3 further comprising a cam drive element disposed adjacent the valve core, the cam drive element comprising a first cam surface engaging the first locking pin and a step feature engageable by the actuator as it approaches the first release position to drive the first locking pin to disengagement from the valve core when the actuator reaches the first release position.

7. The valve of claim 3 in which the actuator comprises a second locking pin engaged with the moveable valve core to lock the valve core in the second stable configuration, the actuator configured to disengage the second locking pin from the valve core upon reaching the second release position, in which the valve core further includes (i) a first pin ramp surface within a channel extending between a first deep end and a first pin-receiving hole at a shallow end and (ii) a second pin ramp surface within a channel extending between a second deep end and a second pin-receiving hole at a shallow end, the first and second pin-receiving holes respectively configured to block further motion of the valve core beyond the respective bistable positions.

8. The valve of claim 1 in which at least one of the first, second and third ports comprises a bore housing and an axially displaceable sealing member within the bore housing having a face seal at one end for engagement with the valve core and a sliding seal for sliding engagement with the bore housing, wherein the sealing member is coupled to be driven from an extended position having said face seal engaged with the valve core when the actuator is in the first position to a retracted position when the actuator moves past the first release position.

9. The valve of claim 8 in which the sealing member is coupled to be driven back to the extended position having said face seal engaged with the valve core as the valve core reaches the second stable configuration.

10. The valve of claim 2 in which at least one of the first, second and third ports comprises a bore housing and an axially displaceable sealing member within the bore housing having a face seal at one end for engagement with the valve core and a sliding seal for sliding engagement with the bore housing, wherein the sealing member is coupled: (i) to be driven from an extended position having said face seal engaged with the valve core when the actuator is in the first position to a retracted position when the actuator moves past the first release position, and (ii) to be driven back to the extended position having said face seal engaged with the valve core as the valve core reaches the second stable configuration; and wherein the sealing member is coupled: (i) to be driven from an extended position having said face seal engaged with the valve core when the actuator is in the second position to the retracted position when the actuator moves past the second release position, and (ii) to be driven back to the extended position having said face seal engaged with the valve core as the valve core reaches the first stable configuration.

11. The valve of claim 8 in which the face seal of the sealing member is biased towards the valve core by a spring bias.

12. The valve of claim 8 in which each of the first, second and third ports comprises a respective said bore housing and axially displaceable sealing member.

13. The valve of claim 8 in which the one or more axially displaceable sealing members are driven by the actuator via a cam drive element disposed adjacent to the valve core.

14. The valve of claim 1 in which the first port is configured for connection to a patient airway maintaining device, and the second and third ports are each configured for connection to a ventilator breathing circuit or breathing assistance device.

15. The valve of claim 14 in which the first port has a 22 mm tapered outer diameter connector surface and the second and third ports each have a 22 mm tapered internal diameter connector surface.

16. The valve of claim 1 further including a ventilation apparatus couplable to at least one of the second and third ports.

17. The valve of claim 1 further including an endotracheal tube couplable to the first port.

18. A method of configuring a breathing assistance apparatus for a patient comprising:

providing a valve according to claim 1 coupling a patient breathing tube to the first port, coupling a first ventilation device to the second port, while the valve is in the first stable configuration, coupling a second ventilation device to the third port;

switching the valve to the second stable configuration; and disconnecting the first ventilation device from the second port.

19. A patient ventilator system comprising the valve of claim 1; and one or both of:

a ventilation apparatus coupled to at least one of the second and third ports; and a breathing tube coupled to the first port.

* * * * *